(12) United States Patent
Kawabe et al.

(10) Patent No.: US 12,325,874 B2
(45) Date of Patent: Jun. 10, 2025

(54) BACTERIUM NUMBER MEASURING METHOD AND BACTERIUM NUMBER MEASURING SYSTEM

(71) Applicants: HITACHI, LTD., Tokyo (JP); University of Toyama, Toyama (JP)

(72) Inventors: Shunsuke Kawabe, Tokyo (JP); Yuichi Uchiho, Tokyo (JP); Hideyuki Noda, Tokyo (JP); Hideki Niimi, Toyama (JP); Atsushi Matsui, Toyama (JP)

(73) Assignee: HITACHI, LTD., Tokyo (JP)

( * ) Notice: Subject to any disclaimer, the term of this patent is extended or adjusted under 35 U.S.C. 154(b) by 884 days.

(21) Appl. No.: 17/224,957

(22) Filed: Apr. 7, 2021

(65) Prior Publication Data

US 2021/0317503 A1     Oct. 14, 2021

(30) Foreign Application Priority Data

Apr. 10, 2020   (JP) ................. 2020-071027

(51) Int. Cl.
| | |
|---|---|
| *C12Q 1/18* | (2006.01) |
| *C12M 1/32* | (2006.01) |
| *C12M 1/34* | (2006.01) |
| *C12M 1/36* | (2006.01) |
| *C12Q 1/06* | (2006.01) |

(52) U.S. Cl.
CPC ............. *C12Q 1/18* (2013.01); *C12M 1/3461* (2013.01); *C12M 1/3476* (2013.01); *C12M 23/12* (2013.01); *C12M 41/36* (2013.01); *C12M 41/48* (2013.01)

(58) Field of Classification Search
CPC .......... C12Q 1/18; C12Q 1/06; C12M 1/3461; C12M 1/3476; C12M 41/36; C12M 41/48
See application file for complete search history.

(56) References Cited

FOREIGN PATENT DOCUMENTS

| | | | | |
|---|---|---|---|---|
| GB | 2059990 A | * | 4/1981 | ............... C12Q 1/06 |
| JP | 2008-086279 A | | 4/2008 | |
| JP | 5063075 B2 | * | 10/2012 | ............... C12M 1/34 |

OTHER PUBLICATIONS

Narsaiah et al. Estimation of total bacteria on mango surface by using ATP bioluminescence. Scientia Horticulturae. 2012;146:159-163.*
Hudzicki J. Kirby-Bauer Disk Diffusion Susceptibility Test Protocol. American Society for Microbiology. 2016;1-23.*
Ashino et al. Predicting the decision making chemicals used for bacterial growth. Scientific Reports. 2019;9(7251):1-11.*
Al-Shyoukh et al. Systematic quantitative characterization of cellular responses induced by multiple signals. BMC Syst Biol. 2011;5(88):1-17.*

* cited by examiner

*Primary Examiner* — Lynn Y Fan
(74) *Attorney, Agent, or Firm* — Procopio, Cory, Hargreaves & Savitch LLP

(57) ABSTRACT

Provided is a bacterium number measuring system comprising a database storing known bacterial growth patterns in advance and an analyzing part. The analyzing part has first cultures containing a bacterial liquid that contains a measurement target bacteria and second cultures being different from the first cultures and containing the bacterial liquid and an antimicrobial drug. The analyzing part performs bacterium number measurement which measures the number of bacteria in the first cultures on a culturing part where culturing has started in the first and second cultures. The analyzing part compares the bacterium number measurement result with the growth curves stored in the database and thereby determines a timing to perform MIC measurement which measures the number of bacteria in the second cultures to determine a minimum inhibitory concentration of the measurement target bacterium. The analyzing part performs the MIC measurement at the thus-determined timing.

13 Claims, 10 Drawing Sheets

BACTERIUM NUMBER MEASURING METHOD AND BACTERIUM NUMBER MEASURING SYSTEM

BACKGROUND OF THE INVENTION

1. Field of the Invention

The present invention relates to a technique for a bacterium number measuring method and a bacterium number measuring system.

2. Description of the Related Art

In order to decide on a proper dose of administration to a patient with a bacterial infection, the drug susceptibility test is conducted on the bacterium to find a minimum inhibitory concentration (hereinafter referred to as MIC). Such drug susceptibility testing is conducted by mixing a bacterium and an antimicrobial drug, culturing the mixture, and evaluating the growth behavior of the bacterium. To evaluate the growth behavior of a bacterium, the number of bacteria needs to be found. Bacterium number measuring methods include, for example, turbidity evaluation using absorbance measurement, evaluation of the amount of adenosine triphosphate (ATP) using chemiluminescence, and direct observation using a microscope.

In recent years, in order to speedily determine MIC, a method for speedily determining MIC, comprising: constantly monitoring the growth behavior; and comparing the growth behavior with a database collected in advance has been proposed. The monitoring is performed at a frequency of several minutes to several tens of minutes.

Such an MIC determination method is disclosed for example in Patent Literature 1. Patent Literature 1 discloses a drug susceptibility evaluation method and microorganism identification method that are characterized as follows: "a method for evaluating drug susceptibility of a target microorganism or tumor cell, the method comprising: preparing a database of growth curves (curve data) obtained by culturing microorganisms whose MICs or tumor cells whose $IC_{50}$ to a drug are known, in cultures of the drug of one or two or more different concentrations; comparing growth curves (curve data) obtained by culturing the target microorganism or tumor cell under the same conditions with the database; obtaining degrees of dissimilarity based on a similarity evaluation method; and determining that the MIC or $IC_{50}$ of a microorganism or tumor cell to the drug with the smallest degree of dissimilarity is the MIC of the target microorganism or the $IC_{50}$ of the target tumor cell" (see Abstract).

PRIOR ART DOCUMENT(S)

Patent Literature(s)

Patent Literature 1: JP 2008-086279 A

As shown in FIG. 13, a bacterium growth period is composed of four phases: a lag phase 401, a logarithmic growth phase 402, a stationary phase 403, and a death phase 404. Among these, the logarithmic growth phase 402 is most susceptible to the effect of an antimicrobial drug and is therefore an important measurement phase for speedy MIC determination. Thus, measuring the number of bacteria at timings other than the logarithmic growth phase 402 does not yield useful information for the MIC determination. The timings of these four phases 401 to 404 differ depending on the bacterial species and strains.

In conventional techniques for MIC determination, the number of bacteria mixed with an antimicrobial drug is measured at certain time intervals, and is compared with a database to determine an MIC. Such determination typically uses a microplate having a plurality of wells (depressions) and measures the number of bacteria in each well. Measuring a single microplate takes at least several minutes. Thus, it is difficult to process a plurality of microplates at the same time, in non-destructive testing such as turbidity measurement or microscopic observation, or in destructive testing such as APT luminescence measurement. Also, measuring the number of bacteria at timings other than the logarithmic growth phase 402 yields no useful information for MIC determination as described earlier, and lowers the accuracy of MIC determination. Also, since the timing of the logarithmic growth phase is different depending on the bacterial species and strains, it is difficult to measure the number of bacteria for the MIC determination with a predetermined period of culturing.

Destructive testing such as, e.g., chemiluminescent measurement or fluorescence emission measurement using ATP or a nucleic acid contained in a bacterium is advantageous in being able to evaluate the number of bacteria with high sensitivity. However, having to destroy bacteria for every measurement, before every measurement of the number of bacteria, destructive testing has to extract and destroy a part of the sample from a culture part where the bacteria is cultured, to measure the number of bacteria. Thus, the measurement cost and cumbersome work increase in proportion to the number of times the measurement is performed.

SUMMARY OF THE INVENTION

The present invention has been made under such circumstances and has an object to enable efficient MIC determination.

To solve the above problem, the present invention provides a bacterium number measuring method comprising causing an analyzing part to perform analysis based on information in a storage part that stores known bacterial growth curves in advance. The analyzing part has a plurality of first cultures each containing a bacterial liquid that contains a measurement target bacteria which is a target bacteria for performing bacterium number measurement and second cultures being different from the first cultures and containing the bacterial liquid and an antimicrobial drug, and performs first measurement which measures the number of bacteria in the first cultures on a culturing part where culturing has been started in the first cultures and the second cultures. The analyzing part compares a result of the first measurement with the growth curves stored in the storage part and thereby determines a timing to perform second measurement which measures the number of bacteria in the second cultures to determine a minimum inhibitory concentration of the measurement target bacterium. The analyzing part performs the second measurement at the timing thus determined.

Other solving means will be described in the embodiments below where appropriate.

The preset invention enables efficient MIC determination.

DETAILED DESCRIPTION OF THE EMBODIMENTS

Next, modes for carrying out the present invention (referred to as "embodiments") will be described in detail with reference to the drawings where necessary.

First Embodiment (Drug Susceptibility Testing System Z)

Figure 1:
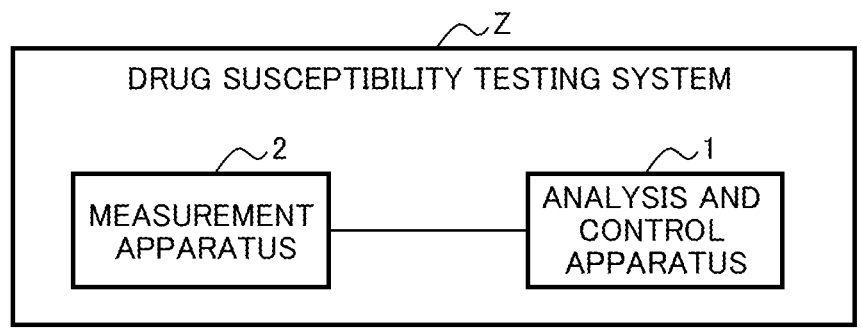
FIG. 1 is a diagram showing an example configuration of a drug susceptibility testing system according to a first embodiment.

FIG. 1 is a diagram showing an example configuration of a drug susceptibility testing system Z according to a first embodiment.

The drug susceptibility testing system Z has a measurement apparatus 2 and an analysis and control apparatus 1.

The measurement apparatus 2 measures the number of bacteria in a microplate 3 (see FIG. 2) (bacterium number measurement), obtains measurement results, and transmits the measurement results to the analysis and control apparatus 1. For the bacterium number measurement, ATP luminescence measurement, turbidity measurement, bacterium number measurement by microscopic observation, or the like is used.

Figure 13:
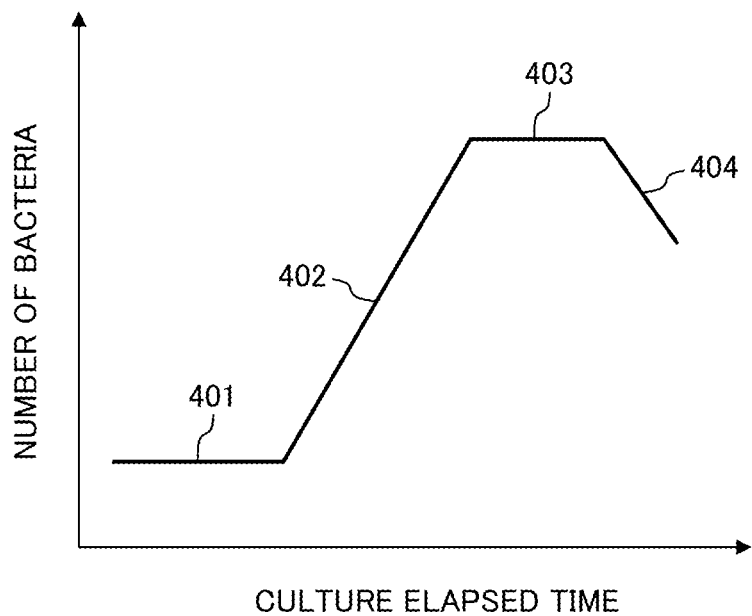
FIG. 13 is a diagram showing a bacterial growth period.

The analysis and control apparatus 1 controls dispensing of a bacterial liquid and an antimicrobial drug to the microplate 3. The analysis and control apparatus 1 also controls bacterium number measurement. Based on the results of bacterium number measurement, the analysis and control apparatus 1 makes a determination of whether a bacteria to be measured (hereinafter referred to as a measurement target bacteria) has transitioned to the logarithmic growth phase 402 (see FIG. 13) and a determination of an MIC. The measurement target bacterium is a target bacterium for performing bacterium number measurement for the MIC determination and is dispensed to the microplate 3.

(Measurement Apparatus 2)

Figure 2:
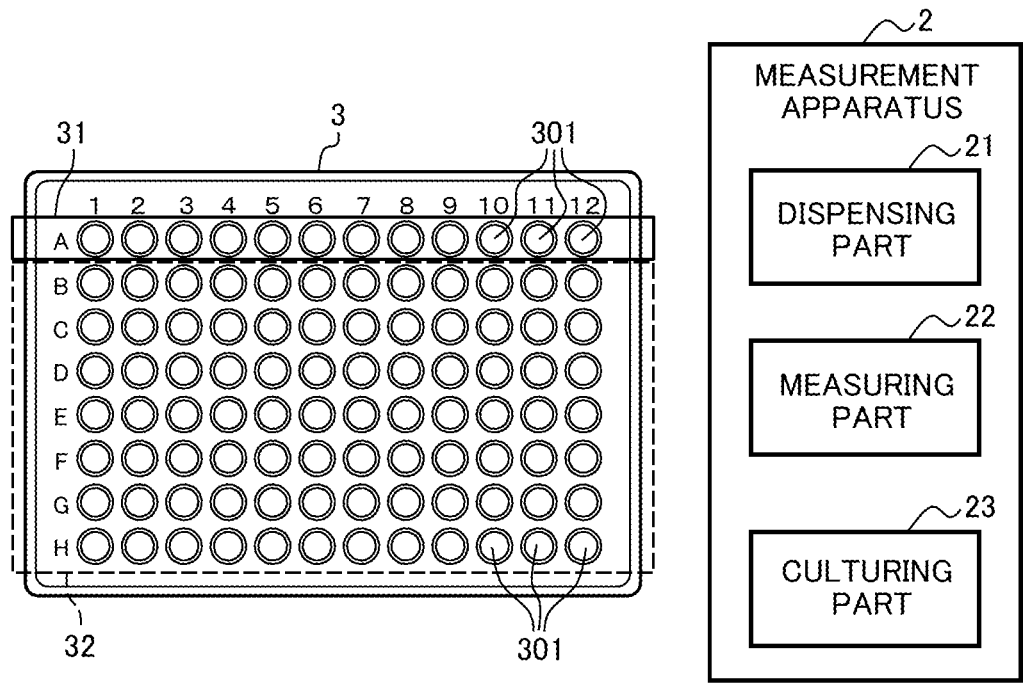
FIG. 2 is a diagram showing an example configuration of a measurement apparatus according to a first embodiment.

FIG. 2 is a diagram showing an example configuration of the measurement apparatus 2 according to the first embodiment.

The measurement apparatus 2 has a dispensing part 21, a measuring part 22, and a culturing part 23.

The dispensing part 21 dispenses a bacterial liquid and an antimicrobial drug to wells 301 (depressions) in the microplate 3.

The measuring part 22 performs bacterium number measurement on the wells 301 of the microplate 3. A description on the wells 301 will be given later. As described earlier, ATP luminescence measurement, turbidity measurement, bacterium number measurement by microscopic observation, or the like is used for the bacterium number measurement.

The culturing part 23 is maintained at a certain temperature. In the culturing part 23, the measurement target bacteria dispensed to the microplate 3 are cultured.

(Analysis and Control Apparatus 1)

Figure 3:
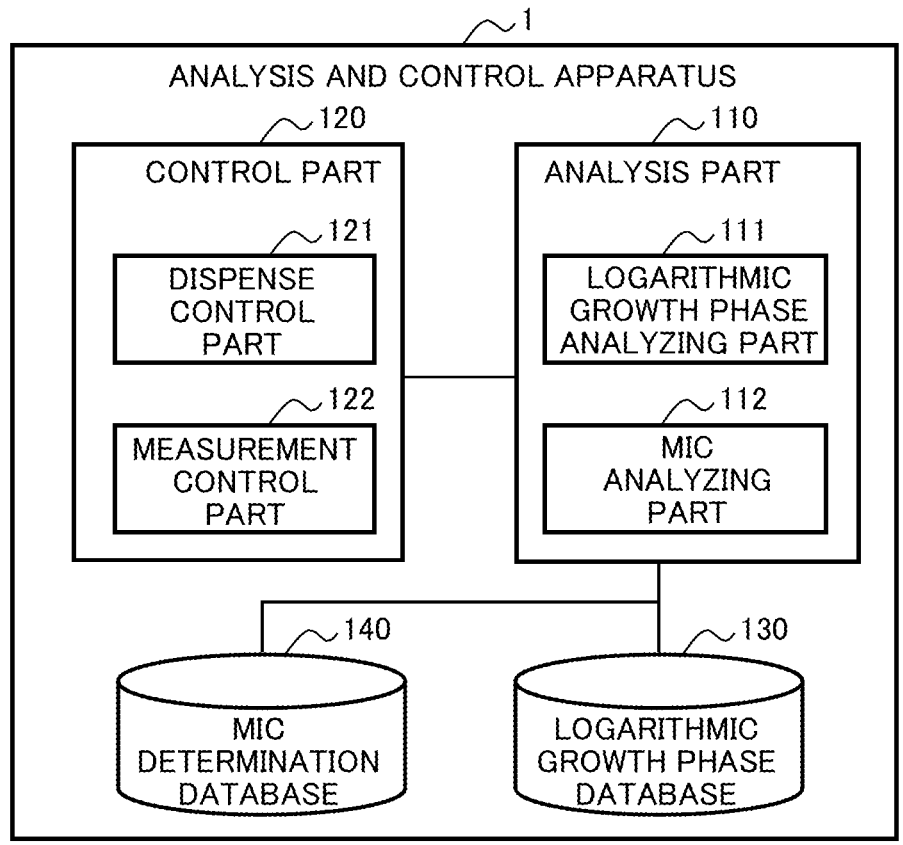
FIG. 3 is a diagram showing an example configuration of an analysis and control apparatus according to the first embodiment.

FIG. 3 is a diagram showing an example configuration of the analysis and control apparatus 1 according to the first embodiment.

The analysis and control apparatus 1 has an analysis part 110, a control part 120, a logarithmic growth phase database 130, and an MIC determination database 140.

Figure 7:
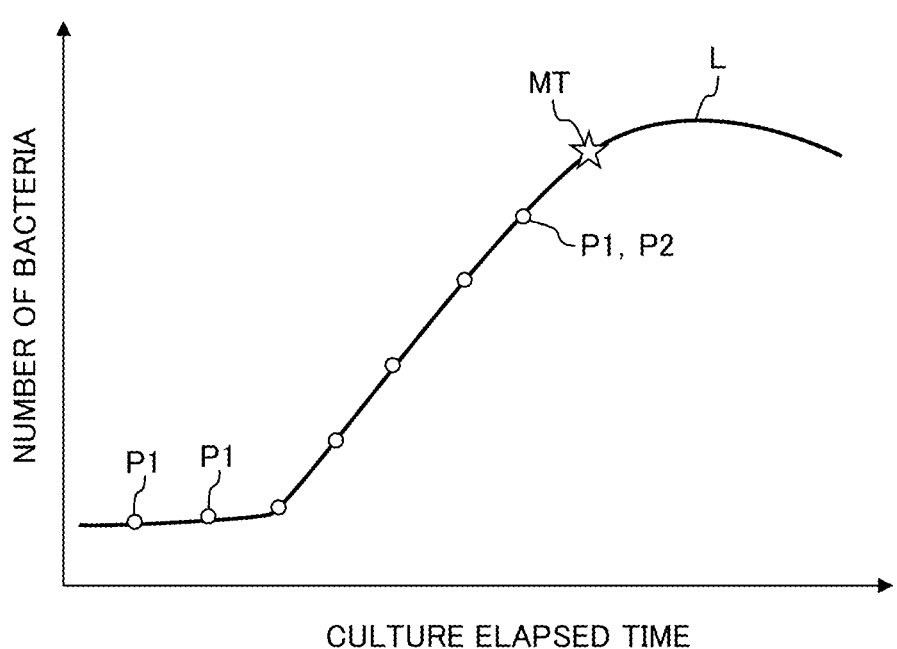
FIG. 7 is a graph showing culture elapsed time on the horizontal axis and the number of bacteria on the vertical axis, according to the first embodiment.

The logarithmic growth phase database 130 stores growth patterns L of various bacterial species (see FIG. 7; growth curves). The logarithmic growth phase database 130 holds, for example, a total of several thousands of patterns of bacterial growth curves (growth patterns L) and minimum inhibitory concentrations acquired in the past. The patterns include, for example, several hundreds of patterns for *Escherichia coli*, several hundreds of patterns for *Staphylococcus aureus*, several hundreds of patterns for *Klebsiella pneumoniae*, and several hundreds of patterns for *Pseudomonas aeruginosa*.

The MIC determination database 140 stores MIC determination data on various bacterial species with respect to a plurality of antimicrobial drugs. Specifically, MIC determination database 140 holds bacterium number data obtained by past MIC determination for each bacterial species and each drug.

The analysis part 110 has a logarithmic growth phase analyzing part 111 and an MIC analyzing part 112.

The logarithmic growth phase analyzing part 111 determines whether the measurement target bacterium dispensed to the microplate 3 has transitioned to the logarithmic growth phase 402 based on the numbers of bacteria measured in respective monitoring wells 31 of the wells 301 in the microplate 3 shown in FIG. 2.

After the logarithmic growth phase analyzing part 111 determines that the measurement target bacterium dispensed to the microplate 3 has transitioned to the logarithmic growth phase 402, the MIC analyzing part 112 has the numbers of bacteria measured at once in the respective MIC determination wells 32 of the wells 301. Here, by "at once" it means measuring the numbers of bacteria in the MIC determination wells 32 of the wells 301 sequentially and successively. Then, based on the results of the bacterium number measurement, the MIC analyzing part 112 determines the MIC of the measurement target bacterium.

Description on the monitoring wells 31 and the MIC determination wells 32 will be given later. Also, in second and third embodiments to be described later, the MIC analyzing part 112 determines the time at which to perform MIC measurement (MIC measurement time). MIC measurement is to measure the numbers of bacteria in the MIC determination wells 32 to determine an MIC.

The control part 120 has a dispense control part 121 and a measurement control part 122.

The dispense control part 121 controls the dispensing part 21 of the measurement apparatus 2 so that the dispensing part 21 dispenses an antimicrobial drug and a bacterial liquid containing a measurement target bacteria to the microplate 3.

The measurement control part 122 controls the measuring part 22 of the measurement apparatus 2 so that the measuring part 22 performs bacterium number measurement on the microplate 3, and the measurement control part 122 acquires the number of bacteria obtained as a result of the bacterium number measurement.

(Hardware Configuration)

Figure 4:
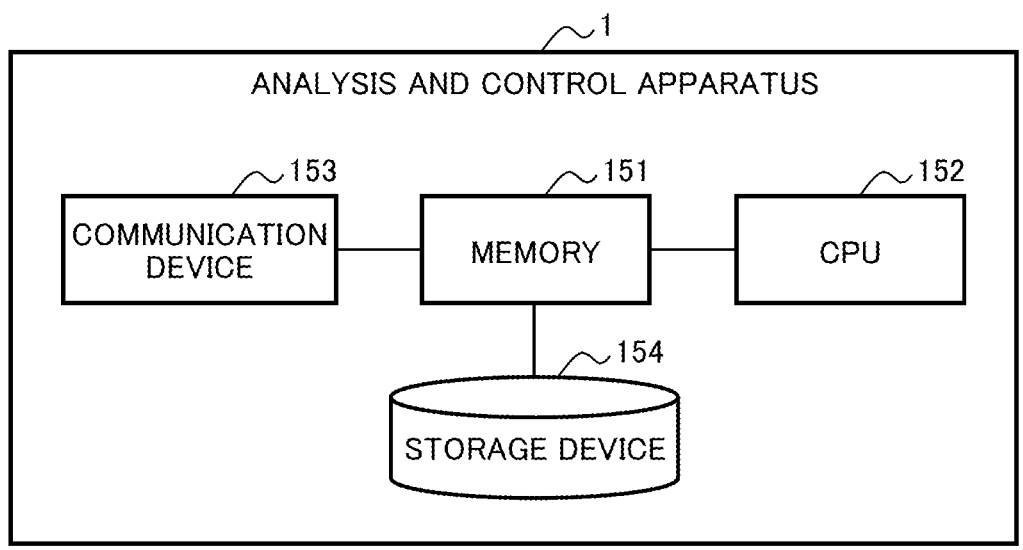
FIG. 4 is a diagram showing the hardware configuration of the analysis and control apparatus.

FIG. 4 is a diagram showing the hardware configuration of the analysis and control apparatus 1.

The analysis and control apparatus 1 has a memory 151, a central processing unit (CPU) 152, a communication device 153, a storage device 154, and other components.

The CPU 152 loads a program stored in the storage device 154 to the memory 151 and executes the program. Thereby, the parts shown in FIG. 3, namely, the analysis part 110, the control part 120, the logarithmic growth phase analyzing part 111 and the MIC analyzing part 112 constituting the analysis part 110, and the dispense control part 121 and the measurement control part 122 constituting the control part 120 are implemented.

The storage device 154 corresponds to the logarithmic growth phase database 130 and the MIC determination database 140 in FIG. 3.

The communication device 153 transmits control commands to the dispensing part 21 of the measurement apparatus 2 and receives bacterium number data from the measuring part 22.

(Flowchart)

Figure 5:
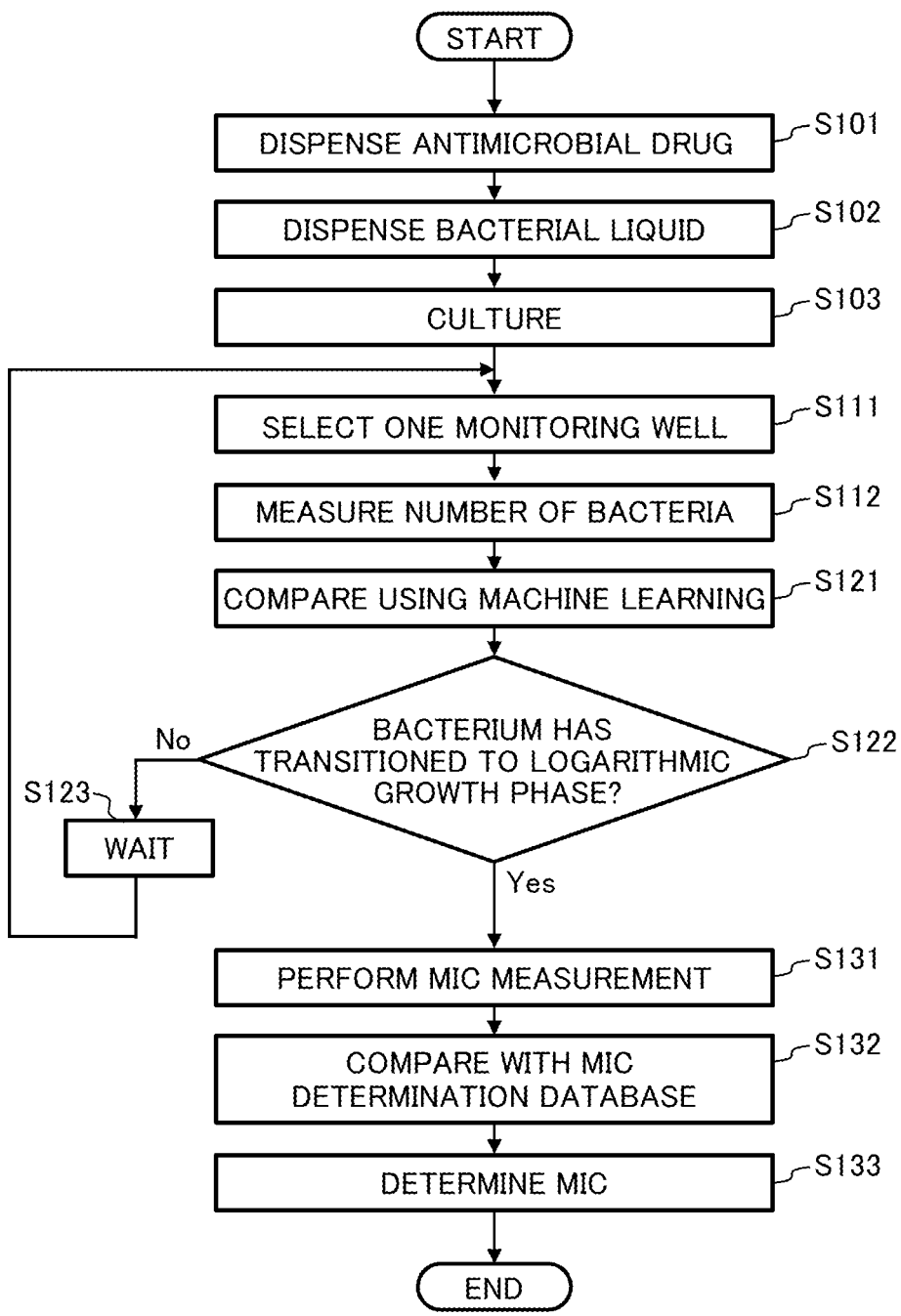
FIG. 5 is a flowchart showing a procedure of MIC determination processing according to the first embodiment.

FIG. 5 is a flowchart showing a procedure of MIC determination processing according to the first embodiment.

First, the dispense control part 121 causes the dispensing part 21 to dispense an antimicrobial drug into the wells 301 of the microplate 3 (see FIG. 6) (S101).

Figure 6:
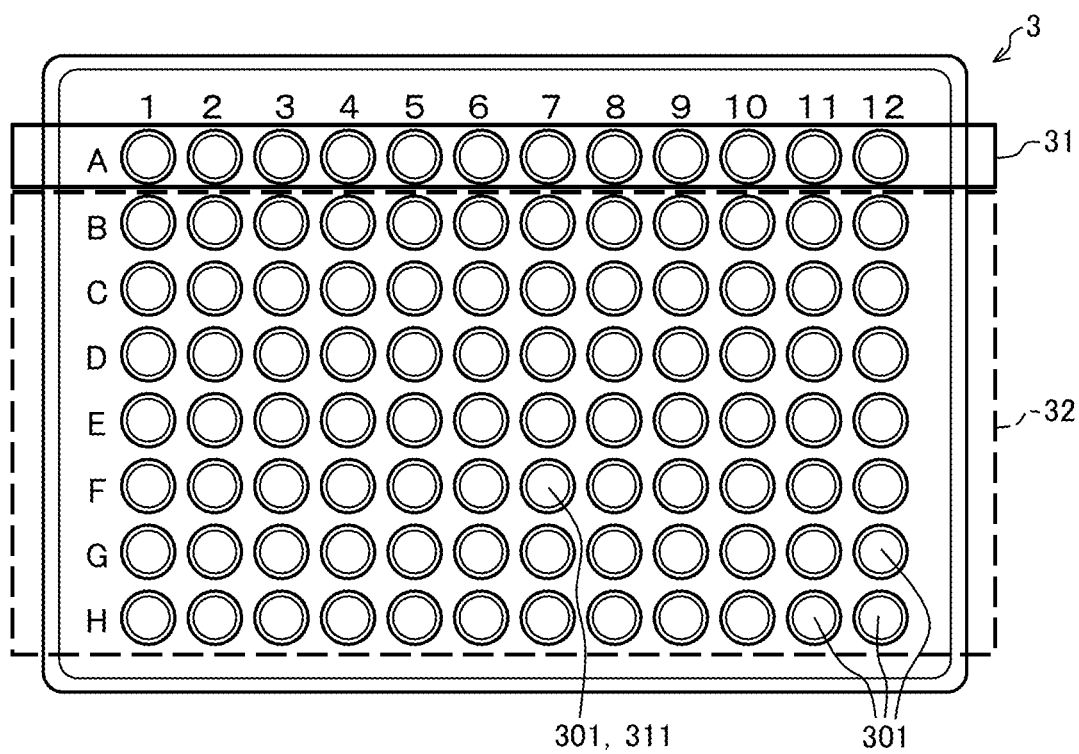
FIG. 6 is a diagram showing a microplate.

With reference to FIG. 6, a description is given on this dispensing of an antimicrobial drug in Step S101.

(Monitoring Wells 31 and MIC Determination Wells 32)

FIG. 6 is a diagram showing the microplate 3.

As shown in FIG. 6, the microplate 3 used in the present embodiment has 12×8=96 wells 301. The wells 301 are depressions into which to dispense a measurement target bacteria and a drug.

As shown in FIG. 6, the columns are assigned numbers "1" to "12," and the rows are assigned letters "A" to "H." Each well 301 is denoted by a combination of the letters "A" to "H" and the numbers "1" to "12." For instance, the well 301 indicated by reference numeral 311 is denoted by "F-7."

The dispensing part 21 dispenses an antimicrobial drug in the following procedure.

First, the dispensing part 21 does not dispense an antimicrobial drug to the wells 301 of "A-1" to "A-12," although a bacterial liquid containing a measurement target bacteria will be dispensed into these wells 301. Such (control) wells 301 of "A-1" to "A-12" into which a bacterial liquid (a measurement target bacteria) is dispensed but no antimicrobial drug is dispensed are referred to as monitoring wells 31. As shown in FIG. 6, the monitoring wells 31 out of the wells 301 are adjacent in a row. In other words, the dispensing part 21 dispenses a bacterial liquid such that the monitoring wells 31 are adjacent. Such alignment allows subsequent processing to be conducted efficiently.

To the wells 301 on the rows "B" to "H," not only an antimicrobial drug but also a bacterial liquid is dispensed. Such wells 301 into which not only an antimicrobial drug but also a bacterial liquid is dispensed are referred to as MIC determination wells 32.

Different antimicrobial drugs are dispensed to the columns "1" to "12," with the concentrations of each antimicrobial drug being different among "B" to "H". For instance, an antimicrobial drug "α" is dispensed to "B-1" to "H-1." In this dispense, the antimicrobial drug "α" of a given dilute concentration is dispensed to "H-1," and the antimicrobial drug "α" of a dilute concentration twice as high as that for "H-1" is dispensed into "G-1." Similarly, the antimicrobial drug "α" of a dilute concentration twice as high as that for "G-1" is dispensed into "F-1," and the antimicrobial drug "α" of a dilute concentration twice as high as that for "F-1" is dispensed into "E-1." In this way, the antimicrobial drugs "α" with doubling dilute concentrations are dispensed to "H-1" to "B-1" in this order.

Similarly, antimicrobial drugs "β" with doubling dilute concentrations are dispensed to the wells 301 of "H-2" to "B-2" in the order of "H-2" to "B-2." The antimicrobial drug "β" is different from the antimicrobial drug "α."

In the same manner, antimicrobial drugs different for the columns are dispensed to the wells 301 of "H-3" to "B-3," "H-4" to "B-4," . . . , "H-12" to "B-12" in the order of "H" to "B," with a dilute concentration being doubled each time.

Although the microplate 3 in FIG. 6 has 12×8=96 wells 301, the number of wells 301 is not limited to this. Also, the microplate 3 is not limited to a rectangular shape, and may be other shapes such as a circular shape. Although only the row "A" is the monitoring wells 31, a plurality of rows, such as the rows "A" and "B," may be the monitoring wells 31. Also, a predetermined column, such as the column "1," may be the monitoring wells 31.

Examples of the antimicrobial drugs used are as follows: in a case where a measurement target bacteria is a Gram-negative bacteria, ampicillin, tazobactam/piperacillin, ceftazidime, cefotaxime, cefepime, ciprofloxacin, levofloxacin, minocycline, amikacin, aztreonam, meropenem, and imipenem; and in a case where a measurement target bacteria is a Gram-positive bacteria, oxacillin, cefazolin, benzylpenicillin, ampicillin, levofloxacin, erythromycin, clindamycin, minocycline, daptomycin, linezolid, vancomycin, and gentamicin. The concentrations of an antimicrobial drug are set so that a breakpoint concentration reported by Clinical and Laboratory Standards Institute (CLSI) may fall within the dilution series.

Referring back to FIG. 5, next, a user prepares a bacterial liquid containing the measurement target bacterium for MIC determination at a bacterial concentration of, for example, $10^5$ CFU/mL, and the dispense control part 121 causes the dispensing part 21 to dispense the prepared bacteria liquid into all the wells 301 in the microplate 3 (S102).

For example, a turbidimeter is used for the adjustment of the bacterial concentration. It is known that when a bacterial liquid adjusted to a 0.5 McFarland unit is diluted 500-fold, its bacterial concentration becomes approximately $10^5$ CFU/mL. For example, cation-adjusted Mueller-Hinton broth is used as the diluent. For example, Gram's stain is used to determine in advance whether the measurement target bacterium for MIC determination is a Gram-negative bacterium or a Gram-positive bacterium. Then, a 100-μL bacterial liquid is dispensed to each of the wells 301 in the microplate 3.

As a result, as described, only a measurement target bacteria is dispensed into the wells 301 on the row "A" ("A-1" to "A-12"), i.e., the monitoring wells 31 as controls, and both an antimicrobial drug and the measurement target bacterium are dispensed into the other wells 301.

Next, culturing is started in the culturing part 23 (S103). The culturing is performed in an environment of, for example, 35° C.

In a certain period of time after the start of the culturing (e.g., five minutes later), the measurement control part 122 selects one of the monitoring wells 31, namely, the wells 301 on the row "A," the number of bacteria in which has yet to be measured (e.g., "A-1") (S111). Then, the measurement control part 122 causes the measuring part 22 to measure the number of bacteria in the selected well 301 (S112). As described, methods used for the bacterium number measurement include ATP luminescence measurement, turbidity measurement, and bacterium number measurement by microscopic observation.

For example, in a case where ATP luminescence measurement is used for the bacterium number measurement, in Step S112 an extraction liquid and a luminescence reagent needed for the ATP luminescence measurement are dispensed into the well 301 selected in Step S111 to perform ATP luminescence measurement. What is used as the luminescence reagent is, for example, CheckLite (registered trademark) HS Set by Kikkoman Biochemifa Company. What is used as the measurement apparatus 2 is, for example, a microplate reader by TECAN (registered trademark) or the like.

Then, the logarithmic growth phase analyzing part 111 refers to the logarithmic growth phase database 130 and performs machine learning of results of the bacterium number measurement performed in Step S112 thus far (S121). The logarithmic growth phase analyzing part 111 uses random forests, a neural network, or the like to extract from the logarithmic growth phase database 130 a growth pattern L (see FIG. 7) that is approximate to the results of the bacterium number measurement performed thus far (i.e., the numbers of bacteria measured). In a case where ATP luminescence measurement is used for the bacterium number measurement, the number of bacteria measured is the amount of light produced by ATP.

Then, the logarithmic growth phase analyzing part 111 determines based on the result in Step S121 whether the growth of the measurement target bacterium has transitioned to the logarithmic growth phase 402 (see FIG. 13) (S122). The logarithmic growth phase analyzing part 111 determines whether the measurement target bacterium has transitioned to the logarithmic growth phase 402 by comparing the extracted growth pattern L with the results of the bacterium number measurement performed thus far (the numbers of bacteria).

If the measurement target bacterium has not transitioned to the logarithmic growth phase (S122→No), the analysis part 110 waits a predetermined period of time (e.g., 20 minutes) (S123) and proceeds back to Step S111.

If the measurement target bacterium has transitioned to the logarithmic growth phase (S122→Yes), the MIC analyzing part 112 causes, via the measurement control part 122, the measuring part 22 to perform MIC measurement on all the MIC determination wells 32 out of the wells 301 at once (S131).

The processing in Step S131 may be performed immediately after it is determined "Yes" in Step S122 or after waiting a predetermined period of time (e.g., 20 minutes) since the determination. In other words, if it is determined "Yes" in Step S122, the MIC analyzing part 112 determines the timing to perform the MIC measurement. As described earlier, MIC measurement is to measure the numbers of bacteria in the MIC determination wells 32 to determine MICs.

Then, the MIC analyzing part 112 compares the results of the MIC measurement performed in Step S131 with the MIC determination database 140 (S132). Thereby, the MIC analyzing part 112 determines an MIC for each antimicrobial drug (S133). The comparing in Step S132 uses machine learning, the method of least square, or the like.

(Measurement Results)

Next, the processing in FIG. 5 is described based on FIG. 7.

FIG. 7 is a graph showing culture elapsed time on the horizontal axis and the number of bacteria (a result of bacterium number measurement) on the vertical axis. In a case where ATP luminescence measurement is used for the bacterium number measurement, the vertical axis represents the amount of light produced by ATP.

Plots P1 each indicate the number of bacteria obtained by the bacterium number measurement performed in Step S112. The growth pattern L is stored in the logarithmic growth phase database 130 in advance.

Every time each plot P1 is obtained, comparing is done using machine learning (Step S121 in FIG. 5).

Then, if it is determined that the bacterium has transitioned to the logarithmic growth phase 402 (see FIG. 13) at the time of a plot P2, MIC measurement and MIC determination processing are performed on the MIC determination wells 32 (Steps S131 and S133 in FIG. 5). Reference sign MT shown in FIG. 7 represents the number of bacteria obtained as a result of the MIC measurement (bacterium number measurement).

(MIC Measurement Results)

Figure 8A:
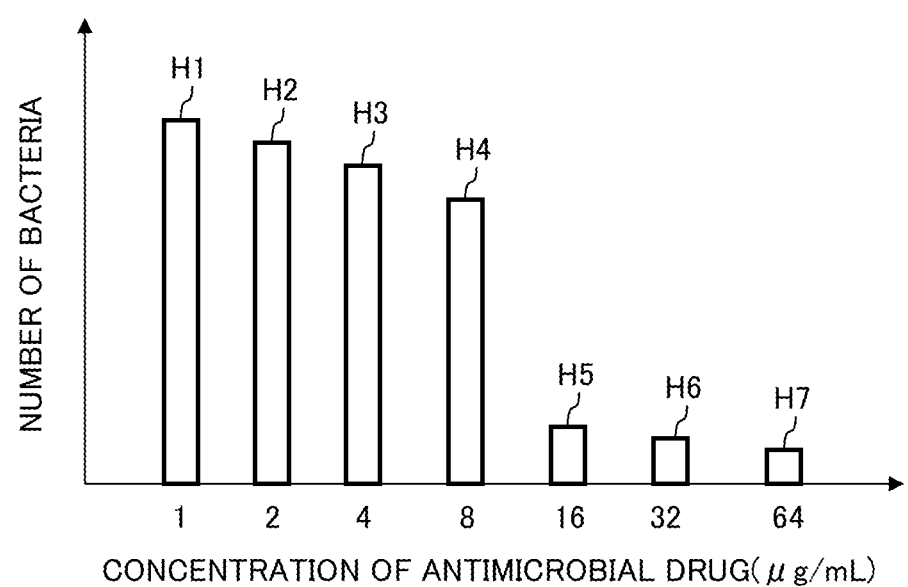
FIG. 8A is a diagram showing the numbers of bacteria in MIC determination wells obtained by MIC measurement using the drug susceptibility testing system of the first embodiment.

FIG. 8A is a diagram showing the numbers of bacteria in the MIC determination wells 32 obtained by the MIC measurement (bacterium number measurement) using the drug susceptibility testing system Z of the present embodiment.

FIG. 8A shows, for example, the numbers of bacteria in the wells 301 of "B-1" to "H-1," with the horizontal axis representing the concentrations of the same antimicrobial drug and the vertical axis representing the number of bacteria. A bin H1 corresponds to the number of bacteria measured for "B-1," and a bin H2 corresponds to the number of bacteria measured for "C-1." Also, a bin H3 corresponds to the number of bacteria measured for "D-1," and a bin H4 corresponds to the number of bacteria measured for "E-1." Likewise, a bin H5 corresponds to the number of bacteria measured for "F-1," a bin H6 corresponds to the number of bacteria measured for "G-1," and a bin H7 corresponds to the number of bacteria measured for "H-1."

As shown in FIG. 8A, the bin H5 ("F-1") exhibits a drastic decrease in the number of bacteria. The MIC analyzing part 112 compares the numbers of bacteria (reference signs H1 to H7) for the respective concentrations with the MIC determination database 140 (Step S132 in FIG. 5) and thereby finds that an antimicrobial concentration of 16 μg/mL is an MIC. As described earlier, an MIC is determined by comparing the numbers of bacteria in the MIC determination wells 32 with the MIC determination database 140 (Step S133 in FIG. 5).

There have heretofore been techniques that use control wells 301 into which no antimicrobial drug is dispensed (or there are also ones with no controls). However, in such prior techniques, control wells 301 are provided to check whether there is contamination by any bacteria other than a measurement target bacteria or to check whether the culture itself is contaminated by any bacteria by dispensing neither an antimicrobial drug nor a bacterium. By contrast, the present embodiment differs from prior techniques in that the monitoring wells 31 are provided to determine whether the bacterium has transitioned to the logarithmic growth phase 402 (see FIG. 13).

In the first embodiment, transition to the logarithmic growth phase 402 is determined using the monitoring wells 31; thus, till the determination on the logarithmic growth phase 402, bacterium number measurement has to be performed on only one of the wells 301 in each microplate 3. Thus, the present embodiment can perform concurrent processing of bacterium number measurement or can increase the number of microplates 3 to be concurrently processed.

Figure 8B:
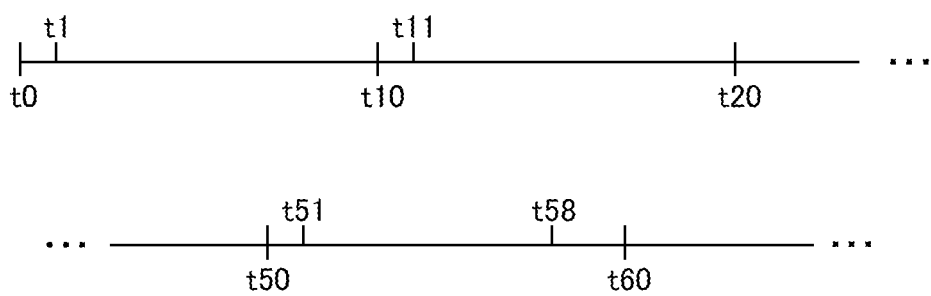
FIG. 8B is a diagram illustrating MIC determination performed by concurrent processing.

This point is further explained with reference to FIG. 8B.

The following assumes that bacterium number measurement has to be performed every 10 minutes and that a time t0 is the start time of the bacterium number measurement, a time t10 is ten minutes after the time t0, and a time t20 is 10 minutes after the time t10. Similarly, times t30, t40, and so on are at 10-minute intervals. Note that FIG. 8B shows only times that are necessary for the illustration.

In prior techniques, whether control wells 301 are provided or not, all the wells 301 in the microplate 3 are measured every time. Thus, the measuring part 22 is continuously occupied a long time for a single microplate 3. For instance, in a case where it takes five seconds to measure the number of bacteria in a single well 301, it takes eight minutes to measure a single microplate 3. In the above-described case where bacterium number measurement has to be performed every ten minutes, bacterium number measurement can be performed only on one microplate 3 between the time t0 and the time t10. Similarly, bacterium number measurement can be performed only on one microplate 3 between the time t10 and the time t20.

By contrast, according to the first embodiment, the monitoring wells 31 are measured one by one until the bacterium is determined as being in the logarithmic growth phase 402. Thus, multiple microplates 3 can be processed concurrently.

Assume that, as described above, it takes five seconds to measure the number of bacteria in one well 301 and that ten microplates 3, namely microplates 3-1 to 3-10, are processed concurrently. Until the bacterium is determined as being in the logarithmic growth phase 402, the numbers of bacteria in the monitoring wells 31 in each microplate 3 are measured one by one. Referring to FIG. 6, the bacterium number measurement is performed in the following order: the well 301 of "A-1" in the microplate 3-1→the well 301 of "A-1" in the microplate 3-2→the well 301 of "A-1" in the microplate 3-3→ . . . →the well 301 of "A-1" in the microplate 3-10. Thus, it takes 50 seconds to measure the numbers of bacteria in the wells 301 of "A-1" in the respective microplate 3-1 to 3-10. Here, with the operation of the measuring part 22 and determination processing as to the transition to the logarithmic growth phase 402 taken into account, the time it takes for the measurement of the numbers of bacteria in the wells 301 of "A-1" in the respective microplates 3-1 to 3-10 and the determination as to the transition to the logarithmic growth phase 402 is set to 60 seconds (=one minute).

Here, the time which is one minute after the time t0 is denoted as t1, the time which is two minutes after the time t0 is denoted as t2, and so on. Likewise, the time which is one minute after the time t10 is denoted as t11, the time which is two minutes after the time t10 is denoted as t12, and so on, and the same definition applies to the following times.

Assume that bacterium number measurement (the first round) for the determination on the logarithmic growth phase 402 is started at the time t0. By the time t1, bacterium number measurement and determination on a transition to the logarithmic growth phase 402 are completed for the wells 301 of "A-1" in all the microplate 3-1 to 3-10 (S111 to 122 in FIG. 5). Assume here that none of the microplate 3-1 to 3-10 is determined as being transitioned to the logarithmic growth phase 402 (S122→"No" in FIG. 5). The analysis part 110 waits (S123 in FIG. 5) until the time t10, at which the next bacterium number measurement is performed.

At the time t10, bacterium number measurement for the determination on a transition to the logarithmic growth phase 402 (the second round) is started. Here, the bacterium number measurement (S112 in FIG. 5) and the determination on a transition to the logarithmic growth phase 402 (S122 in FIG. 5) are performed sequentially on the wells 301 of "A-2" in the microplates 3-1 to 3-10. The bacterium number measurement and the determination on a transition to the logarithmic growth phase 402 are completed at time t11.

The processing goes on in the same manner, and assume that at the time t51 (the fifth round), it is determined that the bacterium in the microplate 3-1 has transitioned to the logarithmic growth phase 402, while no transition to the logarithmic growth phase 402 is observed in the microplate 3-2 to 3-10.

The processing from the MIC measurement to the MIC determination (S131 to S133 in FIG. 5) is performed on the microplate 3-1 the bacterium in which has been determined as now being in the logarithmic growth phase 402. Specifically, the processing from the MIC measurement (S131 in FIG. 5: bacterium number measurement) to the MIC determination (S133 in FIG. 5) is performed on the 84 MIC determination wells 32 of the wells 301 in the microplate 3-1. It takes seven minutes to measure the numbers of bacteria in the 84 MIC determination wells 32 out of the wells 301. Thus, after starting at the time t51 when it is determined that the bacterium in the microplate 3-1 has transitioned to the logarithmic growth phase 402, the bacterium number measurement (MIC measurement) on the MIC determination wells 32 in the microplate 3-1 ends at a time t58. Thus, the bacterium number measurement (MIC measurement) on the MIC determination wells 32 in the microplate 3-1 ends well before the time t60 at which the next bacterium number measurement for the determination on a transition to the logarithmic growth phase 402 will be started for the microplates 3-2 to 3-10.

Then, similar processing is repeated for the microplates 3-2 to 3-10 in which a transition to the logarithmic growth phase 402 has yet to be observed.

In this way, according to the approach of the first embodiment, the determination on the logarithmic growth phase 402 needs only one well 301 per round. Thus, it is possible to drastically increase the number of microplates 3 that can be processed concurrently, as shown in FIG. 8B. The approach of the first embodiment can therefore greatly improve work efficiency. Such effect can be produced whether the bacterium number measurement uses destructive testing or non-destructive testing.

According to the first embodiment, in a case where non-destructive testing is used for the bacterium number measurement, preparing the monitoring wells 31 eliminates the need to take an aliquot of bacterial liquid every time bacterium number measurement is performed for the determination on the logarithmic growth phase 402. This enables decrease in testing costs and mitigation of cumbersome work. In the first embodiment, the growth pattern L stored in the logarithmic growth phase database 130 is compared with results of the bacterium number measurement in Step S112, and the MIC analyzing part 112 determines the timing to perform MIC measurement based on the results of comparing. This enables efficient MIC determination. MICs can be determined efficiently based on results of MIC measurement performed at the timing thus determined.

In addition, according to the first embodiment, MIC measurement is performed if a measurement target bacteria is currently in the logarithmic growth phase 402. This allows proper and efficient MIC determination.

Assume an example where the bacterium number measurement in Step S112 is performed starting from the well 301 of "A-1" and that it is found by the bacterium number measurement on "A-7" that the measurement target bacterium is now in the logarithmic growth phase 402. In this case, bacterium number measurement is not performed on the wells 301 of "A-8" to "A-12." This allows a reduction in the amount of reagent used for the bacterium number measurement.

Second Embodiment

Figure 9:
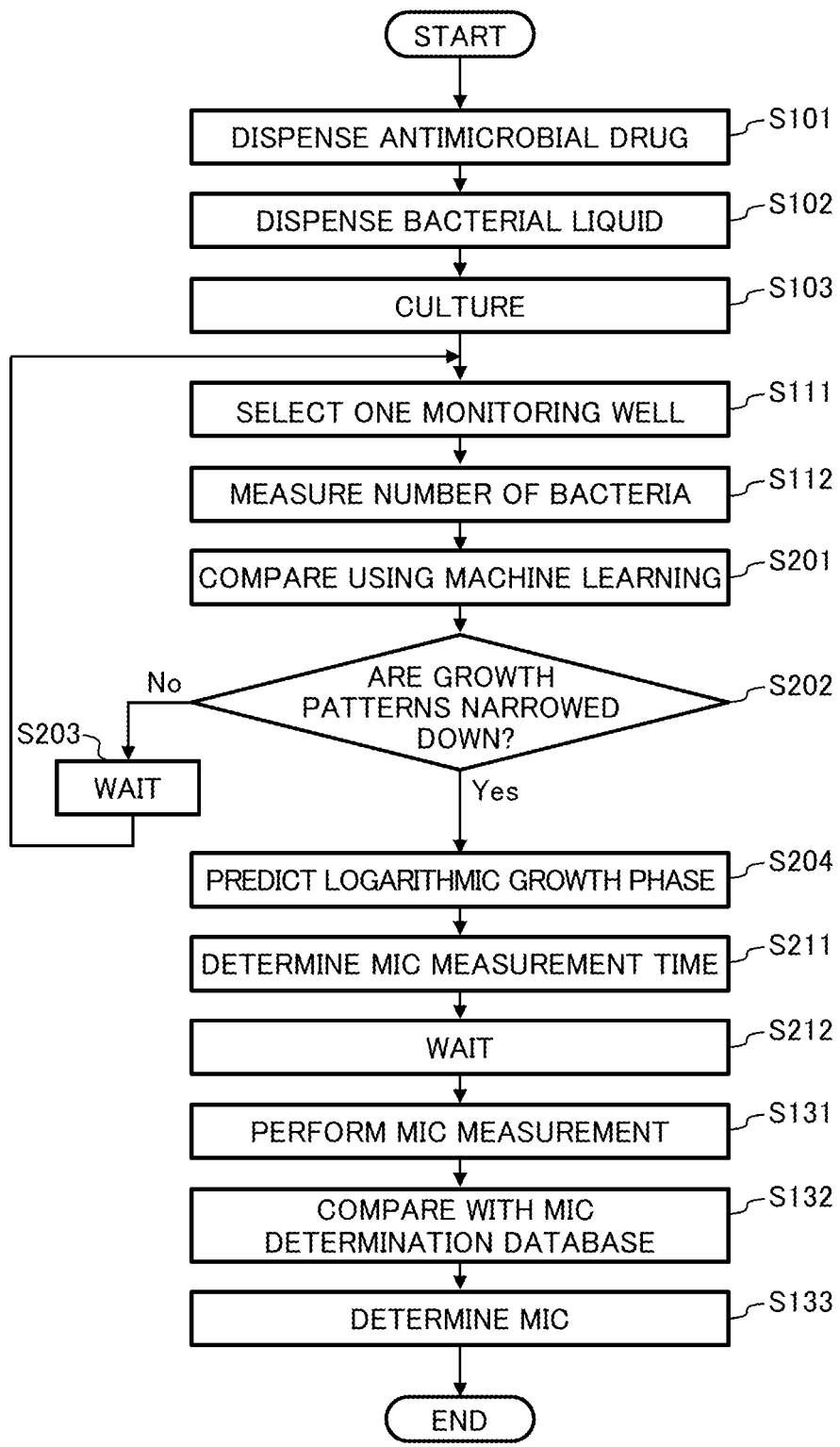
FIG. 9 is a flowchart showing a procedure of MIC determination processing according to a second embodiment.
Figure 10:
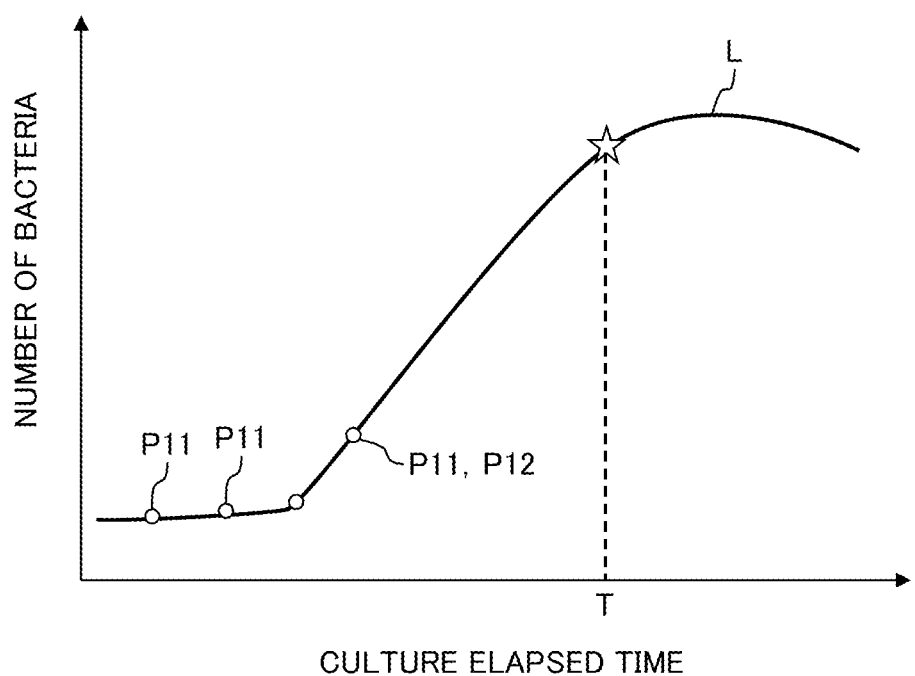
FIG. 10 is a graph showing culture elapsed time on the horizontal axis and the number of bacteria on the vertical axis, according to the second embodiment. A growth pattern L is the same as the one in FIG. 7.

Next, with reference to FIGS. 9 and 10, a second embodiment of the present invention is described.

In the second embodiment, the analysis and control apparatus 1 keeps performing bacterium number measurement only on the monitoring wells 31 (controls) at certain time intervals until the growth characteristics of the measurement target bacterium can be determined. Once the growth characteristics of the measurement target bacterium are determined, the analysis and control apparatus 1 stops the bacterium number measurement altogether and waits. Once a predicted time arrives (well after the measurement target bacterium has transitioned to the logarithmic growth phase 402), bacterium number measurement is performed on all the MIC determination wells 32 of the wells 301 to perform MIC determination.

(Flowchart)

FIG. 9 is a flowchart showing a procedure of MIC determination processing according to the second embodiment. In FIG. 9, the same processing as in FIG. 5 is denoted by the same step number and is not described.

Like in the first embodiment, the logarithmic growth phase database 130 stores, for example, a total of several thousands of patterns of bacterial growth curves (growth patterns L) and minimum inhibitory concentrations acquired in the past. The patterns include, for example, several hundreds of patterns of *Escherichia coli*, several hundreds of patterns of *Staphylococcus aureus*, several hundreds of patterns of *Klebsiella pneumoniae*, and several hundreds of patterns of *Pseudomonas aeruginosa*.

The processing in Steps S101 to S112 is the same as that in FIG. 5.

After Step S112, the logarithmic growth phase analyzing part 111 compares the result of the bacterium number measurement in Step S112 with the logarithmic growth phase database 130 by machine learning (S201). The logarithmic growth phase analyzing part 111 uses machine learning to evaluate to which of the growth patterns L stored in the logarithmic growth phase database 130 the result of the bacterium number measurement is approximate and thereby narrow down (identify) candidate growth patterns L. Decision tree analysis or the like is used for the machine learning.

The logarithmic growth phase analyzing part 111 determines whether the growth patterns L have been narrowed down (identified) by the processing in Step S201 (S202).

If the growth patterns L have not been narrowed down (S202→No), the analysis part 110 waits a certain period of time (e.g., 20 minutes) (S203) and then proceeds back to Step S111.

If the growth patterns L have been narrowed down (S202→Yes), the logarithmic growth phase analyzing part 111 predicts a time when the logarithmic growth phase 402 will be reached based on the identified growth pattern L (S204).

Next, the MIC analyzing part 112 determines a time for MIC measurement based on the logarithmic growth phase 402 reaching time predicted in Step S204 (S211). The time for MIC measurement is a time at which to perform MIC measurement (bacterium number measurement) on the MIC determination wells 32.

Thereafter, the MIC analyzing part 112 waits for the time for MIC measurement to arrive (S212).

Then, Steps S131 to S133, which are the same as those in FIG. 5, are performed.

In the processing in Step S211, if it is found based on the growth patterns L identified in Step S201 that the measurement target bacterium is likely to be a fast-growing bacterium whose doubling time is, for example, 20 to 25 minutes, the MIC analyzing part 112 determines the time for MIC measurement so as to wait two hours after the culture start time. Alternatively, if it is found that the measurement target bacterium is likely to be a slow-growing bacterium whose doubling time is, for example, one hour, the MIC analyzing part 112 determines the time for MIC measurement so as to wait five hours after the culture start time.

(Measurement Results)

Next, the processing in FIG. 9 is described based on FIG. 10.

FIG. 10 is a graph showing culture elapsed time on the horizontal axis and the number of bacteria (a result of bacterium number measurement) on the vertical axis. The growth pattern L is the same as the one in FIG. 7.

Plots P11 each indicate the number of bacteria obtained by the bacterium number measurement performed in Step S112. Every time each plot P11 is obtained, comparing is done using machine learning (Step S202 in FIG. 9).

Then, assume that the growth pattern L is identified at a plot P12 (Step S202→Yes in FIG. 9). Then, the MIC analyzing part 112 calculates an MIC measurement time T based on the identified growth pattern L (Step S211 in FIG. 9).

According to the second embodiment, the MIC measurement time is determined once the growth pattern L of the measurement target bacterium is found out, so as not to perform bacterium number measurement until the MIC measurement time. This allows reductions in unnecessary measurement time and the amount of reagent used for the bacterium number measurement. Thus, like in the first embodiment, concurrent processing of multiple microplates 3 and cost reduction are possible. Especially when ATP luminescence measurement is used for the bacterium number measurement, the amount of reagent used for the ATP luminescence measurement can be reduced.

Third Embodiment

Next, a third embodiment of the present invention is described with reference to FIGS. 11A, 11B, and 12.

In the third embodiment, the logarithmic growth phase analyzing part 111 performs bacterium number measurement on the monitoring wells 31 only a bare minimum number of times necessary for determining the growth characteristics of the measurement target bacterium. Then, once the growth characteristics are determined, the analysis part 110 stops performing the bacterium number measurement on the monitoring wells 31, and once the MIC measurement time arrives, performs bacterium number measurement on all the MIC determination wells 32 and performs MIC determination.

(Flowchart)

Figure 11A:
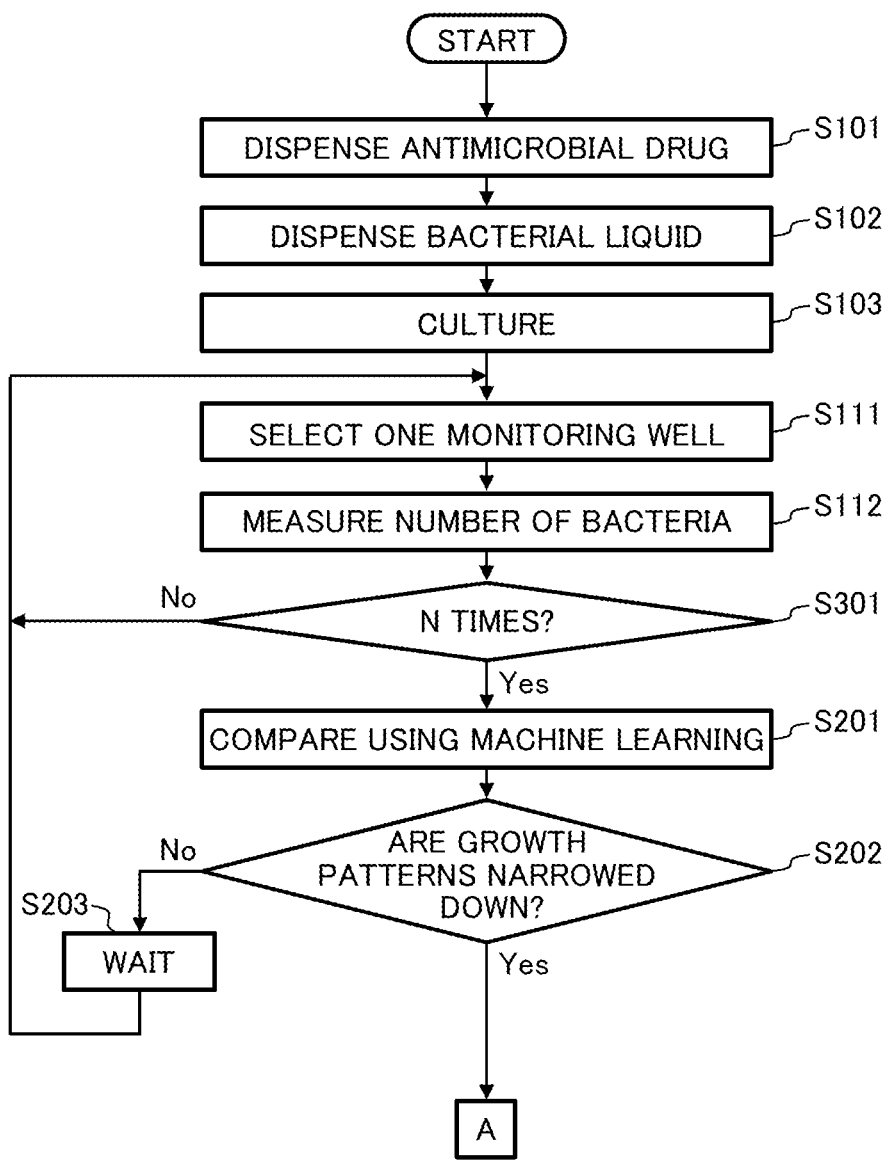
FIG. 11A is a flowchart showing a procedure of MIC determination processing according to a third embodiment (part 1).
Figure 11B:
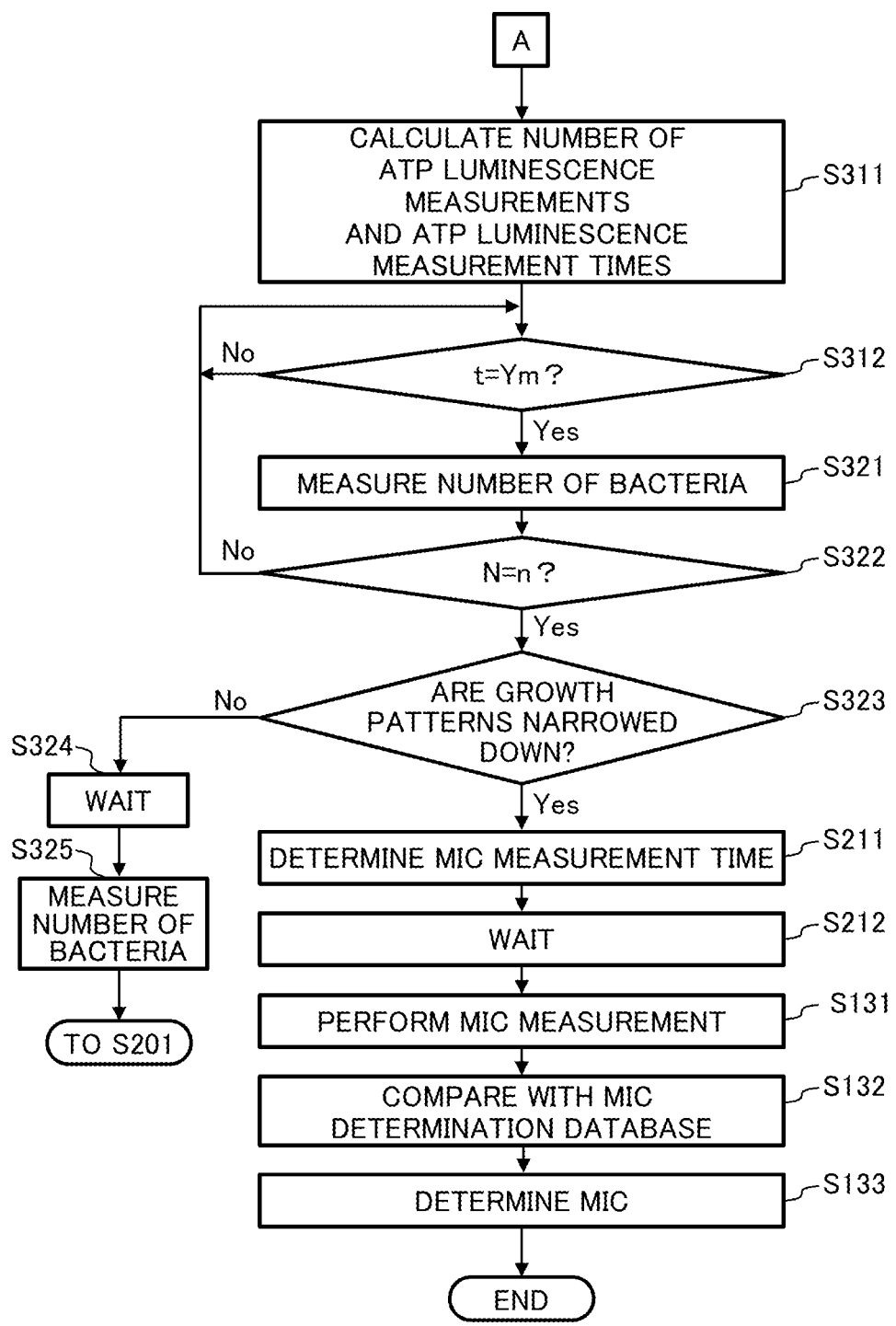
FIG. 11B is a flowchart showing a procedure of the MIC determination processing according to the third embodiment (part 2).

FIGS. 11A and 11B are each a flowchart showing a procedure of MIC determination processing according to the third embodiment. In FIGS. 11A and 11B, the same processing as that in FIGS. 5 and 9 is denoted by the same step number and is not described.

Further, like in the first embodiment, the logarithmic growth phase database 130 stores, for example, a total of several thousands of patterns of bacterial growth curves (growth patterns L) and minimum inhibitory concentrations acquired in the past. The patterns include, for example, several hundreds of patterns of *Escherichia coli*, several hundreds of patterns of *Staphylococcus aureus*, several hundreds of patterns of *Klebsiella pneumoniae*, and several hundreds of patterns of *Pseudomonas aeruginosa*.

Steps S101 to S112 in FIG. 11A are the same as those in FIG. 9.

After Step S112, the logarithmic growth phase analyzing part 111 determines whether the number of bacteria is n times or more the number of bacteria measured initially (S301). The number of bacteria can be calculated from a result of bacterium number measurement (i.e., the number of bacteria). The value of n depends on the bacteria species estimated by Gram's stain, a mass analyzer, or the like before the testing. Here, n=2.

If the number of bacteria is below n times (S301→No), the analysis part 110 proceeds back to Step S111.

If the number of bacteria is n times or more (S301→Yes), the analysis part 110 proceeds to Step S201.

In Step S201 in the third embodiment, the characteristics of a bacterial species are estimated by machine learning, comparing "the number of bacteria inoculated" and "the time it takes to double" with the logarithmic growth phase database 130. The growth patterns L are thereby narrowed down. For example, decision tree analysis or the like is used for the machine learning. The control apparatus determines a period of time T1 till the next bacterium number measurement based on the estimated growth patterns L. For example, the period of time T1 is one hour for a fast-growing bacterium and is three hours for a slow-growing bacterium. Even in a case where a bacterial species dispensed is already known prior to the testing as a result of mass analysis, genetic testing, or the like, growth pattern estimation is performed anew here since each bacterial strain grows at a different speed.

Then, after it is determined "Yes" in Step S202, the number of times n to perform additional bacterium number measurements and bacterium number measurement times Y1 to Yn at which to perform the respective additional bacterium number measurements are calculated based on the identified growth patterns L to further narrow down the growth patterns L (S311 in FIG. 11B).

For example, if the growth patterns L are narrowed down to those of fast-growing bacteria in Steps S202 and S203, the logarithmic growth phase analyzing part 111 calculates that the bacterium number measurement should be performed on the monitoring wells 31 every 20 minutes, a total of four times. If the growth patterns L are narrowed down to those of slow-growing bacteria in Steps S202 and S203, the logarithmic growth phase analyzing part 111 calculates that the bacterium number measurement should be performed on the monitoring wells 31 every 40 minutes, a total of three times.

Then, the logarithmic growth phase analyzing part 111 determines whether the current time t is any one of the bacterium number measurement times Ym (m=1 to n) calculated in Step S311 (S312).

If the current time t is none of the bacterium number measurement times Ym (m=1 to n) (S312→No), the analysis part 110 proceeds back to Step S312.

If the current time t is any one of the bacterium number measurement times Ym (m=1 to n) (S312→Yes), the logarithmic growth phase analyzing part 111 performs bacterium number measurement on a monitoring well 31 the number of bacteria in which has yet to be measured (S321).

Then, the logarithmic growth phase analyzing part 111 determines whether the number of times N Step S321 has been performed is equal to the number of times n of bacterium number measurements calculated in Step S311 (S322).

If N is not equal to n (S322→No), the analysis part 110 proceeds back to Step S312.

If N is equal to n (S322→Yes), the logarithmic growth phase analyzing part 111 compares the results of bacterium number measurement in Steps S112 and S321 with the growth patterns L identified in Steps S201 and S202 and determines whether the growth patterns L have been completely narrowed down (identified) (S323).

If the growth patterns L have not been narrowed down (S323→No), after a wait for a predetermined period of time (e.g., 20 minutes) (S324), bacterium number measurement is performed on a monitoring well 31 the number of bacteria in which has yet to be measured (S325). Thereafter, the analysis part 110 proceeds back to Step S201. For example, assume a case where although a bacterium is thought to be a fast-growing one at first, the possibility that the bacterium is a slow-growing one arises as a result of bacterium number measurement performed anew. In such a case, the number of times n of bacterium number measurement and their bacterium number measurement times Y1 to Yn are calculated again.

If the growth patterns L have been narrowed down (S323→Yes), the MIC measurement time is determined based on the identified growth pattern L (S211).

Processing performed after that is the same as that in FIG. 9, and is therefore not described here.

(Measurement Results)

Figure 12:
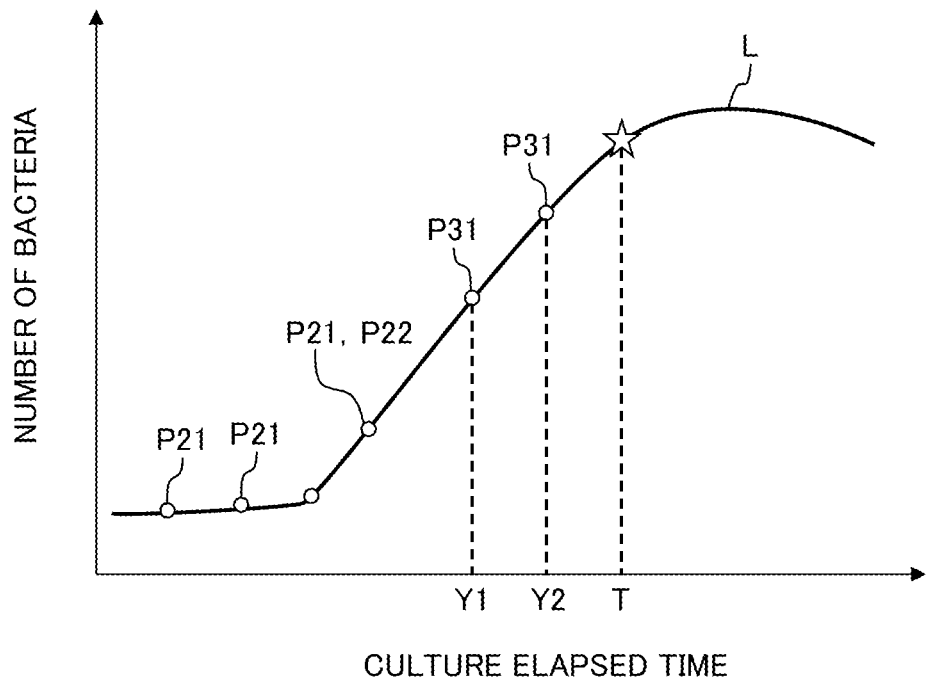
FIG. 12 is a graph showing culture elapsed time on the horizontal axis and the number of bacteria on the vertical axis, according to the third embodiment.

Next, the processing in FIGS. 11A and 11B is described based on FIG. 12.

FIG. 12 is a graph showing culture elapsed time on the horizontal axis and the number of bacteria (a result of bacterium number measurement) on the vertical axis. The growth pattern L is the same as the one in FIG. 7.

Plots P31 each indicate the number of bacteria obtained by the bacterium number measurement performed in Step S112.

Then, assume that the growth pattern L is identified at a plot P32 (Step S202→Yes in FIG. 9).

Here, the logarithmic growth phase analyzing part 111 calculates bacterium number measurement times Y1 and Y2 to perform bacterium number measurement for conformation. After confirming that results of bacterium number measurement performed at the bacterium number measurement times Y1 and Y2 (plots P33) are on the growth pattern L, the MIC analyzing part 112 calculates the MIC measurement time T based on this growth pattern L.

According to the third embodiment, when it is found that a measurement target bacteria is likely to be a slow-growing bacteria such as *Pseudomonas aeruginosa*, the measuring intervals for monitoring are set long to avoid monitoring at an unnecessarily high frequency. Accordingly, the number of times to perform bacterium number measurement on the monitoring wells 31 can be reduced. This allows the reagent used for the bacterium number measurement to be consumed less, which in turn allows cost reduction. Also, reducing the number of times of unnecessary monitoring allows, like in the first embodiment, more microplates 3 to be processed concurrently in the same drug susceptibility testing system Z. Note that monitoring means bacterium number measurement on the monitoring wells 31.

A bacterium number measuring method used in the present embodiment is, as described earlier, ATP luminescence measurement, turbidity measurement, bacterium number measurement by microscopic observation, or the like. However, methods other than the above may be used. For example, non-destructive testing methods usable for the bacterium number measurement include autofluorescence measurement, spectrometry, electrical detection using an electrical resistance value or the like, and detection using extrabacterial metabolites. Destructive testing methods usable for the bacterium number measurement include detection using intrabacterial metabolites or enzymes specific to the bacterium, detection using nucleic acid (i.e., genes), and detection using fluorescence emission from bacterial genes or protein.

In Step S301 in the third embodiment, the logarithmic growth phase analyzing part 111 determines whether the number of bacteria is n times or more the number of bacteria measured initially. However, the present invention is not limited to this, and the logarithmic growth phase analyzing part 111 may determine whether bacterium number measurement has been performed a predetermined number of times.

Although decision tree analysis is used for the machine leaning used in Steps S121 and 201 in the present embodiment, regression analysis, clustering analysis, a neural network, or the like may be used instead. Also, for the bacterium number measurement performed in Steps S112, S131, S321, S325, the same method may be used, or a different method may be used in at least one of the steps.

The analysis and control apparatus 1 does not have to have the logarithmic growth phase database 130 thereinside and may be able to access the logarithmic growth phase database 130 in a cloud (not shown). Similarly, the analysis and control apparatus 1 does not have to have the MIC determination database 140 thereinside and may be able to access the MIC determination database 140 in a cloud (not shown).

The present invention is not limited to the embodiments described above and includes various modifications. For instance, the above embodiments are described in detail to illustrate the prevent invention in an easy-to-understand way, and the present invention is not necessarily limited to a mode including all the features described. A feature in a configuration in one embodiment may be replaced with a configuration in another embodiment, or a configuration in one embodiment may be added with a configuration in another embodiment. Also, a feature in a configuration in each embodiment may be deleted, replaced, or added with a different configuration.

The configurations, functions, the parts 110 to 112, 120 to 122, the storage device 154, and the like described above may be partly or entirely implemented by hardware by, for example, designing of an integrated circuit. Also, as shown in FIG. 4, the configurations, functions, and the like described above may be implemented by software by a processor such as the CPU 152 interpreting and executing programs for implementing the functions. The programs for implementing the functions and information such as tables and files may be stored in a hard disk (HD), or may be stored in the memory 151, a recording device such as a solid-state drive (SSD), or a recording medium such as an integrated circuit (IC) card, a Secure Digital (SD) card, or a Digital Versatile Disc (DVD).

In each of the embodiments, control lines and information lines shown are ones deemed necessary for illustration, and not all the control lines and information lines of a product are necessarily shown. In actuality, almost all the configurations are connected to one another.

What is claimed is:

1. A bacterium number measuring method, comprising:
    causing an analyzing part to perform measurement analysis based on information in a storage part that stores known bacterial growth curves in advance, wherein
    the analyzing part has a plurality of first cultures each containing a bacterial liquid that contains a measurement target bacteria which is a target bacteria for performing bacterium number measurement and second cultures being different from the first cultures and containing the bacterial liquid and an antimicrobial drug, and performs first measurement which measures the number of bacteria in the first cultures on a culturing part where culturing has been started in the first cultures and the second cultures,
    in performing the measurement analysis, the analyzing part compares a result of the first measurement with the growth curves stored in the storage part and thereby determines a timing to perform second measurement which measures the number of bacteria in the second cultures to determine a minimum inhibitory concentration of the measurement target bacterium,
    the analyzing part performs the second measurement at the timing thus determined,
    comparing the result of the first measurement with the growth curves uses machine learning based on one of regression analysis, clustering analysis, and a neural network, and
    at least one of the first measurement and the second measurement is a measurement using fluorescence emission from genes or protein of the measurement target bacterium.

2. The bacterium number measuring method according to claim 1, wherein
    the analyzing part performs the second measurement if determining as a result of comparing the result of the first measurement with the growth curves stored in the storage part that the measurement target bacterium has transitioned to a logarithmic growth phase.

3. The bacterium number measuring method according to claim 1, wherein the analyzing part compares the result of the first measurement with the growth curves of a plurality of bacterium stored in the storage part and, based on the growth curve identified as a growth curve of the measurement target bacteria, the analyzing part calculates a second measurement time at which to perform the second measurement, and the analyzing part performs the second measurement after waiting until the second measurement time thus calculated.

4. The bacterium number measuring method according to claim 1, wherein the analyzing part compares the result of the first measurement with the growth curves of a plurality of bacterium stored in the storage part and, the analyzing part calculates the number of times to perform the first measurement additionally to confirm that the growth curve is the growth curve of the measurement target bacterium, when a growth curve of the measurement target bacteria is identified as a result of additionally performing the first measurement the number of times calculated and comparing results of the first measurement with the growth curves stored in the storage part again, the analyzing part calculates a second measurement time at which to perform the second measurement based on the identified growth curve, and the analyzing part performs the second measurement after waiting until the second measurement time calculated.

5. The bacterium number measuring method according to claim 1, wherein the analyzing part determines the minimum inhibitory concentration of the measurement target bacterium based on a result of the second measurement.

6. The bacterium number measuring method according to claim 1, wherein an other one of the first measurement and the second measurement is a measurement using chemiluminescence including ATP chemiluminescence.

7. The bacterium number measuring method according to claim 1, wherein an other one of the first measurement and the second measurement is a measurement using non-destructive testing, including turbidity measurement and bacterium number measurement by microscopic observation.

8. The bacterium number measuring method according to claim 1, wherein the analyzing part performs the first measurement a plurality of times until the timing to perform second measurement is determined, and stops the first measurement once the timing to perform second measurement is determined.

9. The bacterium number measuring method according to claim 1, wherein the first measurement and the second measurement use a same measurement method.

10. The bacterium number measuring method according to claim 1, wherein the first measurement and the second measurement use different measurement methods.

11. The bacterium number measuring method according to claim 1, wherein the machine learning is based on the regression analysis.

12. The bacterium number measuring method according to claim 1, wherein the machine learning is based on the clustering analysis.

13. The bacterium number measuring method according to claim 1, wherein the machine learning is based on the neural network.

* * * * *

UNITED STATES PATENT AND TRADEMARK OFFICE
CERTIFICATE OF CORRECTION

| | | |
|---|---|---|
| PATENT NO. | : 12,325,874 B2 | Page 1 of 1 |
| APPLICATION NO. | : 17/224957 | |
| DATED | : June 10, 2025 | |
| INVENTOR(S) | : Shunsuke Kawabe et al. | |

It is certified that error appears in the above-identified patent and that said Letters Patent is hereby corrected as shown below:

On the Title Page

In item (73), after HITACHI, LTD., Tokyo (JP), insert --UNIVERSITY OF TOYAMA, Toyama (JP)--

Signed and Sealed this
Thirtieth Day of September, 2025

John A. Squires
*Director of the United States Patent and Trademark Office*